United States Patent [19]

Braatz et al.

[11] Patent Number: 4,514,506

[45] Date of Patent: Apr. 30, 1985

[54] METHOD FOR THE IDENTIFICATION AND PURIFICATION OF HUMAN LUNG TUMOR-ASSOCIATED ANTIGENS (HLTAA) AND CLINICAL DETECTION AND DETERMINATION OF THESE ANTIGENS

[75] Inventors: James A. Braatz, Beltsville; Kenneth R. McIntire, Kensington; Gerald L. Princler, Frederick, all of Md.

[73] Assignee: The Government of the United States as represented by the Secretary of the Department of Health and Human Services, Washington, D.C.

[21] Appl. No.: 462,022

[22] Filed: Jan. 28, 1983

Related U.S. Application Data

[63] Continuation-in-part of Ser. No. 351,588, Feb. 23, 1982.

[51] Int. Cl.³ .................... G01N 33/54; G01N 33/56; G01N 33/58
[52] U.S. Cl. .................... 436/518; 436/531; 436/536; 436/538; 436/540; 436/542; 436/543; 436/544; 436/545; 436/546; 436/547; 436/804; 436/808; 436/813; 260/112 R; 435/7; 424/88
[58] Field of Search ........ 436/503, 504, 518, 536–542, 436/543–547, 63, 64, 804, 808, 813, 823, 824; 260/112 R; 424/85, 88, 95, 177; 435/4, 7, 810; 206/569

[56] References Cited

PUBLICATIONS

Braatz, J. A. et al., Cancer Research, vol. 42, pp. 849–855, (3–1982).
Princler, G. L. et al., Cancer Research, vol. 42, pp. 843–848 (3–1982).
Braatz, J. A. et al., Federation Proceedings, vol. 41 (3), Abstract 2120 (1982).
Braatz, J. A. et al., Oncodevelopmental Biology and Medicine, vol. 3, pp. 169–177 (1982).
Braatz, J. A. et al., Cancer Research, vol. 43, pp. 110–113 (1–1983).
McIntire, K. R. et al., Carcino-Embryonic Proteins, vol. II, pp. 533–540 (1979).
Gaffar, S. A. et al., J. Biological Chemistry, vol. 254 (6), pp. 2097–2102 (1979).
Braatz, J. A. et al., J. National Cancer Institute, vol. 61 (4), pp. 1035–1046 (1978).
Gaffar, S. A. et al., J. Biological Chemistry, vol. 255 (17), pp. 8334–8339 (1980).
McIntire, K. R., Proceedings of the Serono Symposia, vol. 46, pp. 95–109 (1982).
Braatz, J. A. et al., Federation Proceedings, vol. 40 (6), p. 1737, Abstract 1139 (1981).
Princler, G. L. et al., Amer. Assoc. Cancer Research Abstracts, vol. 22, p. 21, Abstract 84 (1981).
Braatz, J. A. et al., Oncodevelopmental Biology and Medicine, vol. 2 (5), p. 54 Abstract 107 (1981).
Rosenberg, Steven A., Serological Analysis of Human Cancer Antigens, pp. 181–196, Braatz, J. A. et al. (1980).
Sega, E. et al., J. National Cancer Institute, vol. 62, pp. 1125–1130 (1979).
McIntire, K. R., Progress in Cancer Research and Therapy, vol. II, pp. 183–189 (1979).
Maxim, P. E. et al., Federation Proceedings, vol. 37 (6), p. 1485, Abstract 1185 (1978).
Veltri, R. W. et al., Cancer Research, vol. 37, pp. 1313–1322 (1977).

Primary Examiner—Benjamin R. Padgett
Assistant Examiner—M. Moskowitz
Attorney, Agent, or Firm—Holman & Stern

[57] ABSTRACT

The invention comprises a method for the purification of a human lung tumor-associated antigen (hLTAA) specific to human lung tumors of diverse histological characteristics; serum levels of hLTAA correlate with lung tumor incidence, and appear to usefully discriminate between various stages of the malignancies. The invention further comprises an immunoassay predicated on purified hLTAA for the detection and quantitative determination of hLTAA in biological fluids, particularly blood serum, and diagnostic systems for clinical immunoassay procedures.

17 Claims, 19 Drawing Figures

METHOD FOR THE IDENTIFICATION AND PURIFICATION OF HUMAN LUNG TUMOR-ASSOCIATED ANTIGENS (HLTAA) AND CLINICAL DETECTION AND DETERMINATION OF THESE ANTIGENS

This is a continuation-in-part of U.S. patent application Ser. No. 351,588 filed Feb. 23, 1982.

BACKGROUND OF THE INVENTION

Immunologic approaches to cancer management have focussed in recent years on attempts to identify and isolate human tumor-associated antigens which will prove clinically useful in the immunodiagnosis of cancer. While it is well known in theory that malignant tumors can be detected by radioimmunoassay (RIA) techniques for associated cell-surface antigens, the theory is limited in its practical clinical application to malignant tumors for which specific cell-surface antigens are available in highly purified form; also, these antigens must be released into the bloodstream, and the determinants must retain antigenicity when radiolabelled. Further, clinical utility of the RIA in cancer management is dependent upon biological fluid levels of the selected antigen which substantially correlate with tumor burden; utility is further enhanced if the selected antigen is site-specfic, i.e., associated with tumors of specific organs.

As a result of the difficulties encountered in attempting to isolate and study a protein for which no function or activity is known, and for which the method of isolation relies on the presumption that it is more prevalent in tumor tissues than in normal tissues, satisfactory clinical antigenic markers have not been heretofore characterized for many malignant tumors, in particular, human lung tumors.

SUMMARY OF THE INVENTION

The invention comprises a method for the purification of a human lung tumor-associated antigen (hLTAA) specific to human lung tumors of diverse histological characteristics; serum levels of hLTAA correlate with lung tumor incidence, and appear to usefully discriminate between various stages of the malignancies. The invention further comprises an immunoassay predicated on purified hLTAA for the detection and quantitative determination of hLTAA in biological fluids, particularly blood serum, and diagnostic systems for clinical immunoassay procedures.

DETAILED DESCRIPTION OF THE INVENTION

The clinical marker antigen of the invention (hLTAA) comprising two (2) components designated human lung tumor-associated antigen I and II (hLTAA I and hLTAA II) is purified according to the method of the invention by affinity immunoadsorption from a crude extract of lung tumor source material, preferably after resolution of the crude extract into fractions of high antigenic activity by conventional non-specific procedures such as ion-exchange chromatography and/or gel filtration. The affinity matrix comprises the IgG fraction of an adsorbed xenoantiserum raised against a pool of crude lung tumor extract. Preferably, at all stages of purification, the product is assayed for hLTAA, as by radialimmunodiffusion (RID) against purified antibody. The product antigen, purified hLTAA, is useful in clinical immunoassay procedures according to the present invention for detecting and quantitating serum levels of hLTAA, particularly concentrations below about 1 μg/ml which are typically encountered in clinical applications.

Useful lung tumor extract source material for hLTAA, comprises human tumor extract of the four major histologic types: small cell and squamous carcinoma, large cell undifferentiated carcinoma, and adenocarcinoma. The crude tumor extract is purified by affinity immunoadsorption against an affinity matrix of purified antibody, derived from antisera raised in heterologous species animals such as rabbits or goats against these carcinoma extracts. These antisera develop hLTAA-specific antibodies which are purifiable by conventional adsorption techniques against extracts of normal adult and fetal lung tissue, other normal tissue, and malignant tumors of organs other than lung.

Various immunoadsorption techniques are suitable for purification of hLTAA from crude tumor extract. In an exemplary immunoadsorption procedures, hLTAA antibody is covalently coupled to a solid support such as agarose gels, especially SEPHAROSE gels, or porous glass or polyacrylamide beads by known methods, and antigen is removed from solution by complexing with the immunoadsorbent. hLTAA is thereafter dissociated from anti-hLTAA by customary dissociation agents such as ammonium or potassium thiocyanate, potassium iodide, urea, or propanoic acid. Preferably, the crude tumor extract is treated prior to affinity immunoadsorption to reduce the protein complexity of the extracted material. Suitable pretreatment procedures include ion-exchange chromatography, which separates proteins on basis of electrostatic binding capacity, and gel filtration, which separates proteins on the basis of size. Detailed descriptions of these and other non-specific protein separation procedures useful for resolution of protein mixtures are found in many texts, for example, Garvey, et al., *Method in Immunology,* 3rd ed., published by W. A. Benjamin, Inc., Reading, Mass. (1977). After each purification step, the product is monitored for the presence of hLTAA. Standard RID techniques are useful, employing as standard serial dilutions of the source material or purified antigen.

In the purification process exemplified, purification is accomplished by sequential DEAE cellulose chromatography, gel filtration and affinity immunoadsorption. The proteins obtained by ion exchange chromatography appear heterogenous, with immunological reactivity detected in three different peaks; however, all the active components were immunologically identical, producing lines of identity in Ouchterlony analysis. Gel filtration of the major antigenic component from DEAE-cellulose similarly demonstrated a further fractionation into several active, immunologically identical forms. These results suggest a charge/size isomeric relationship among the various forms, all of which possess a common and identical antigenic site. The major component was isolated throughout the purification scheme. The final product representing 9% of the input activity, produced a single, though broad, protein-staining region on 7% polyacrylamide gels, which was coincident with the antigen in the crude extract as well as with that in an extract from another lung tumor. The relatively low recovery is partially attributable to the subdivision of activity at various steps of purification. The total activity recovered during the affinity immunoadsorption step was 20% of that in the crude extract. Recoveries of 75, 50 and 68% were obtained from DEAE, gel filtration, and immunoadsorption, respectively. The antigen was undetectable by the Ouchterlony technique in the sera of lung cancer patients, indicating a circulating level of <1 µg/ml.

Two immunoreactive forms of hLTAA were observed and isolated after electrophoresis of labelled antigen in 7% polyacrylamide gels. These components, referred to as hLTAA-I and hLTAA-II, in order of mobility, were both judged homogenous and characterized by gel electrophoresis, Sephadex gel filtration, size exclusion high performance liquid chromatography (HPLC) and by sedimentation velocity analysis. The latter three techniques produce identical profiles for both forms of the hLTAA. Sephadex chromatography and HPLC analyses indicated the mass of the antigen, assuming a globular configuration, to be approximately 140,000–150,000 daltons with a $D_{20,w}$ of $4.2-4.3\times10^{-7}$ cm$^2$s$^{-1}$. The $s_{20,w}$ values for both were 4.5–4.6 S. Sodium dodecyl sulfate (SDS) gel electrophoresis of hLTAA-II gave a single component of $M_r=81,700$ while hLTAA-I had a major component identical in size to hLTAA-II, and two minor components of $M_r=50,00$ and 27,700. The observed $M_r$ was independent of the concentration of the acrylamide, indicating that very little, if any, carbohydrate is associated with the antigen; both forms failed to bind to a series of insolubilized lectin columns.

The SDS gel electrophoresis indicated a high degree of purity for hLTAA-II. The sum of the sizes of the two minor peaks from hLTAA-I very closely approximates the size of the major component, suggesting the occurrence of proteolytic cleavage at one site, producing two fragments. Peptide mapping of hLTAA-I and hLTAA-II show a high degree of overlap between the patterns, indicating that these two forms are structurally very similar. The isoelectric point of hLTAA-II (peaks at pH 2.6 and 3.2) generally was more acidic than hLTAA-I (major component entered at pH 4.7, minor component at pH 3.1).

Because of the difficulties in converting results from gel filtration analysis of unknown proteins into reliable $M_r$ estimates, the diffusion coefficient of hLTAA was also calculated, which permitted a calculation of the Stokes radius, which is more reliably related to the behavior of proteins on gel filtration. Thus, the value of 51 Å obtained by this calculation can be considered a more accurate reflection of the size of the antigen, whereas the value of 140,000–150,000 daltons, although less reliable, is useful in initial comparisons which can be made between laboratories involved in similar studies.

Purified hLTAA is generally useful in a known radioimmunoassay. Immunoassays according to the invention are particularly useful for detecting and quantitating levels of hLTAA below about 1 µg/ml, which are undetectable by methods such as Ouchterlony analysis. Since serum levels below 1 µg/ml have been found by the process of the present to be those most commonly associated with the presence of lung tumors. Ouchterlony and related procedures of similar sensitivity are not clinically useful. In a particular embodiment, an immunoassay of the invention broadly comprises a radioimmunoassay employing radio-labelled purified hLTAA and anti-hLTAA in known amount as an assay mixture for serum analysis for hLTAA. Bound-labelled hLTAA is recovered from the test serum, and the concentration compared to a standard curve correlating the concentration of unlabelled competitor antigen with the concentration of bound radioactive antigen. Serum concentration of hLTAA is then employed as an aid in the diagnosis of tumor burden.

In an alternate embodiment, the immunoassay of the invention comprises a solid-phase radioimmunoassay technique of the type based on the SANDWICH principle. In this assay, patient serum or plasma is incubated with a solid support such as a disc containing coupled anti-hLTAA (e.g., goat). Subsequently, radiolabelled anti-hLTAA (e.g. equine) is added, which binds to any hLTAA which has reacted with anti-hLTAA coupled to the support. The complex gives a radioactivity measurement which is compared to a standard curve to give the level of hLTAA in the specimen.

Figure 1:
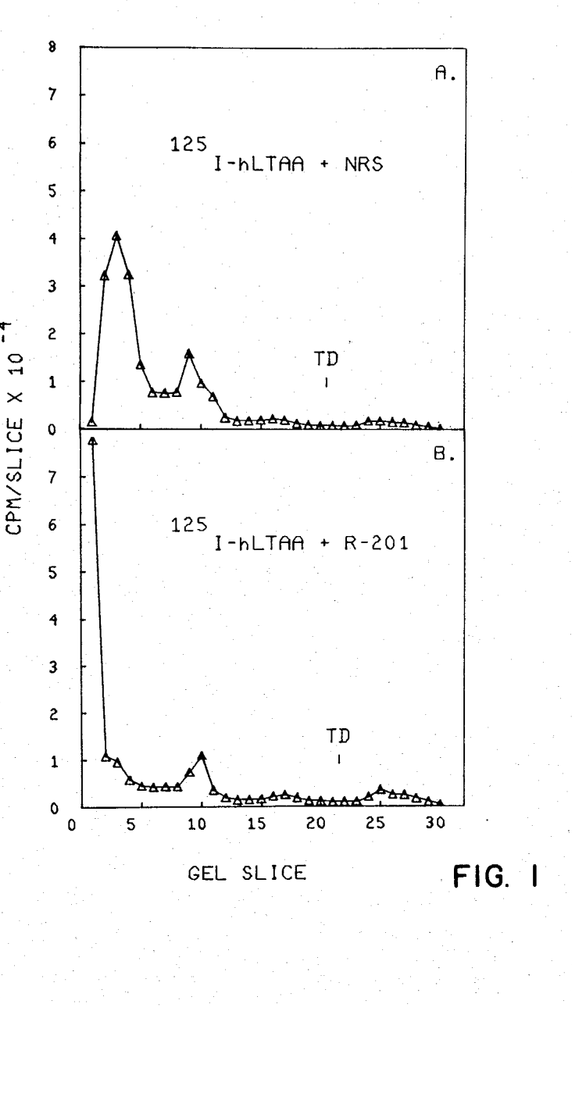
FIG. 1 is a graphic representation of radioiodinated antigen (pool 1 of FIG. 4) incubated 16 h at 4° C. in the presence of 5 μl normal rabbit serum (NRS) (panel A) or 5 μl R-201 (panel B) and then electrophoresed on 7% polyacrylamide gels. The recovery of radioactivity was 98% in A and 82% in B. TD=bromphenol blue tracking dye.
Figure 2:
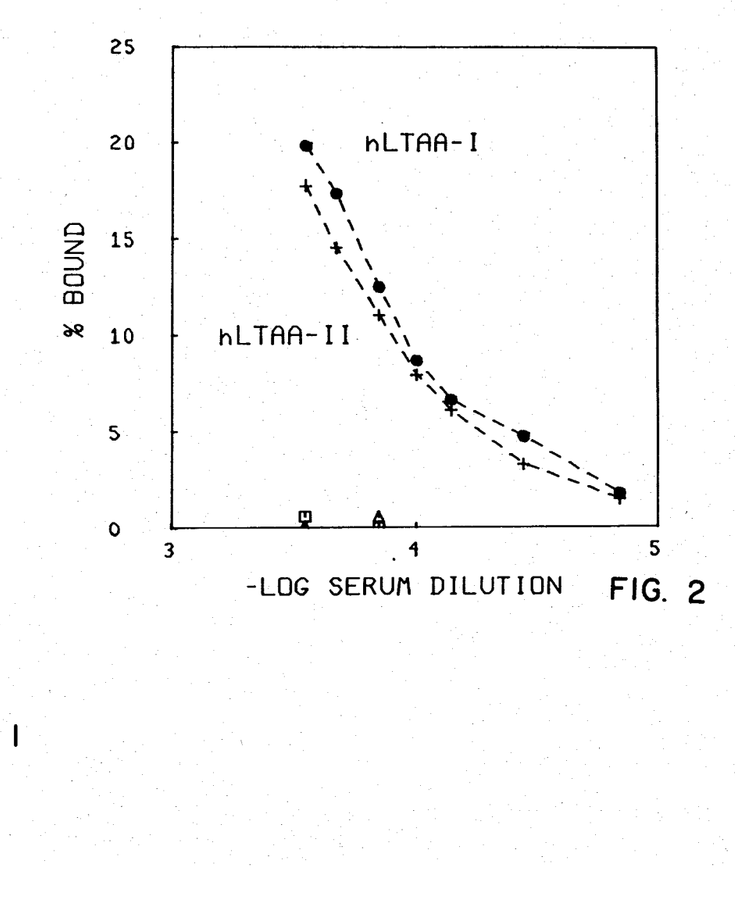
FIG. 2 is a graphic representation of the binding of individual components, hLTAA-I and hLTAA-II to immune serum. Shown are $^{125}$I-hLTAA-I binding to R-201 (● --- ●) and antiserum to $\alpha_1$-antichymostrypsin (□); and $^{125}$I-hLTAA-II binding to R-201 (+----+) and anttiserum to $\alpha_1$-antichymotrypsin (Δ). Free and antibody bound antigen were separated using Pansorbin. Binding in the presence of normal serum was subtracted.

Radioimmunoassays with a useful detection range from 1–100 ng/ml, were developed with hLTAA-I for clinical use. Evaluation of binding of radioiodinated antigen to antibody showed that 20% of the radioiodinated antigen was bound at an antiserum dilution of 1:3500 (FIG. 2). Quantitative binding occurred at higher antibody concentrations, as shown in FIG. 1, which graphically represents a study wherein the major component (which contains both hLTAA-I and hLTAA-II) was completely excluded in the presence of immune serum. In another experiment (FIG. 2), using iodinated hLTAA-I, R-201 at a final dilution of 1:2000, and a second antibody (goat anti-rabbit IgG) in place of Pansorbin to separate free from bound antigen, 96% of the radiolabelled antigen was found to be reactive with the antibody.

Many additional immunoassay procedures well-known to those skilled in the art may be based on the hLTAA and anti-hLTAA of the present invention, such as enzymatic radioisotope assays (ERIA), ultrasensitive enzymatic radioimmunoassays (USERIA), and enzyme potentiated radioimmunoassay (EPRIA). Broadly, various heterogenous enzyme immunoassay systems such as EIA, ELIA, ELISA, CELIA and IEIA are contemplated, as well as assays employing fluorescents as markers. Various radioactive isotopes such as $^{125}$I are employed as the radiolabel.

Conventional antisera are a customary source of antibodies for bioassay procedures according to the present invention; goat antiserum containing antibodies to hLTAA is on deposit at the American Type Culture Collection, Rockville, Md. identified by ATCC accession number 40057. However, monoclonal antibodies having the desired specificity to the antigen are the reagents of choice in many immunological applications, particularly sensitive radioimmunoassays.

Monoclonal antibodies (McAb) useful in the detection and evaluation of hLTAA are obtained from selected hybrid myelomas produced according to well-known protocols. Broadly, hybrid cell cultures produced by fusion of myeloma with cell spleen cells producing the desired antibody are screened to isolate hybrids which produce McAb of the desired specificity, and the selected hybrids cloned. In contrast to conventional antisera which generally contain a mixture of antibodies of varying avidity and specificity monoclonal antibodies secreted by a single hybrid clone are homogeneous, thus providing accurate and reliable assay results. Further, they are relatively inexpensive to produce once a clone has been identified, generally being propagated in tissue culture or mice. The need for large animals or humans as a source of conventional antisera is thus obviated.

The presence of hLTAA in most lung tumor extracts of all histologic types and its absence at significant levels from all normal tissues tested (as measured by double diffusion analysis), qualifies it as a useful lung tumor marker. Since there is no known satisfactory marker for the screening or diagnosis of lung cancer, the hLTAA described here has particular relevance. The development of radioimmunoassays with a sensitivity of 100–1000 times greater than double diffusion assays permits the assay of sera to determine the presence of hLTAA. Further, the quantitation of hLTAA present in sera permits at least a preliminary evaluation of the degree of tumor burden, and may prove to reliably permit discrimination between Stage I and Stage III tumors as well as to permit a reliable prognosis following medical intervention by surgery or medical therapy. Practical applications include the screening of sera of populations at high risk of lung cancer, such as smokers and asbestos workers.

EXAMPLES

I. Identification and Purification of hLTAA from a Primary Lung Tumor

A. Materials

Cyanogen bromide-activated Sepharose 4B, Protein A-Sepharose and Sephadex G-200 were purchased from Pharmacia Fine Chemicals, Piscataway, N.J., and DEAE-cellulose was obtained from Whatman, Inc., Clifton, N.J. Agarose was obtained from L'Industrie Biologique Francaise, S.A., Gennevilliers, France. All chemicals were the best grades commercially available.

B. Methods

1. *Lung Tumor Extraction*—Primary tumor and metastasis to the liver, from a patient with small cell carcinoma of the lung, were combined, giving a total weight of 1657 g. This pool of tissue is referred to herein as LT-120. The tissue was cut into 0.5 inch cubes, divided into eight (8) portions, and 275 ml PBS was added to each. The tissue was disrupted by two 30 s full-power bursts in a Brinkman Polytron homogenizer, using a PT-35 generator. The homogenate was centrifuged for 1 h at 16,300×g in a Sorvall GSA rotor. The supernatants were poured through a gauze filter, combined and stored at −20° C. A second pool of tissue, designated LT-37 was obtained in a similar manner, and found to have immunologic identity with pool LT-120 within the scope of the invention.

2. *Antisera*—Rabbit antisera, designated R-152 and R-201, were obtained according to Braatz, et al., *Purification and Characterization of a Human Lung Tumor-Associated Antigen*, J. Natl. Cancer Inst., 61:1035–1046, 1978. The R-152 and R-201 antisera were raised against a pool of lung tumor extract having immunological identity with the LT-120 and LT-37 pools, as confirmed by double diffusion in gel resolutions showing detection of the same antigenic determinants by these antisera.

These adsorbed antisera detected a protein in 84 of 98 lung tumor extracts and 1 of 13 extracts of tumors from organs other than lung, but were negative, at the level of sensitivity of the double immunodiffusion test, with normal lung extracts, normal tissues, fetal tissues and normal serum.

Figure 3:
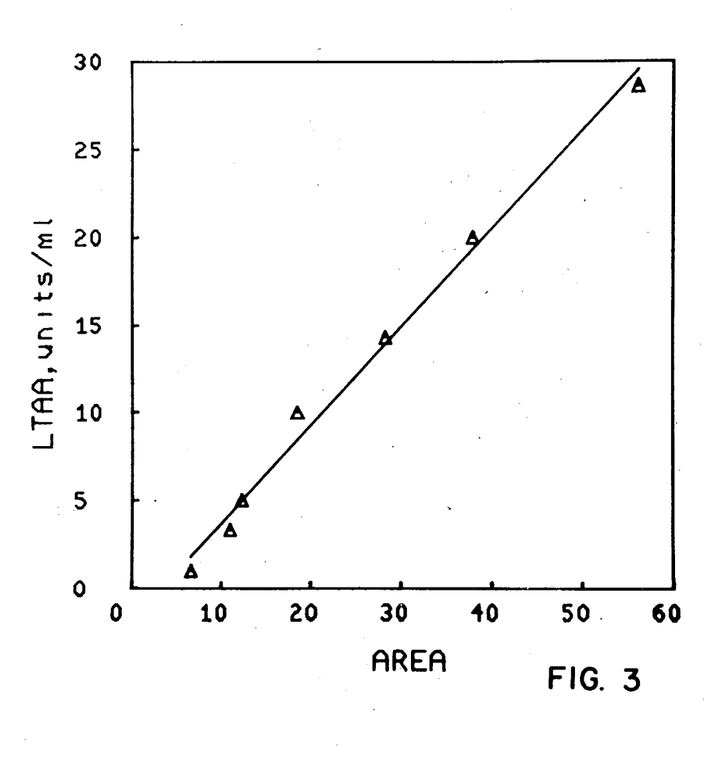
FIG. 3 is a graphic representation of a radialimmunodiffusion assay for hLTAA. Glass slides were coated with 1% agarose containing a fiftyfold dilution of R-152 IgG. Dilutions of a standard lung tumor extract, LT-37, were applied to wells in the plate and allowed to diffuse for at least 42 h. An example of the plate appearance is shown in the photograph on the right. Dilutions of LT-37, at 1.0, 3.3, 5.0, 10.0, 14.3, 20.0 and 28.6 units/ml, are shown in ascending order in the photograph. Area is expressed as $mm^2$.

3. *hLTAA Assay*—A radial immunodiffusion (RID) test was used to quantitate hLTAA after each purification step. The test was similar to that described by Mancini (Mancini, et al., *Immunological Quantitation of Antigens by Single Radial Immunodiffusion*, Immunochem., 2:235–254, 1965) and Fahey and McElvey (Fahey, et al., *Quantitative Determination of Serum Immunoglobulins in Antibody-Agar Plates*, J. Immunol., 94:84–90, 1965). The IgG fraction from rabbit antiserum R-152 was isolated by precipitation with 45% $(NH_4)_2SO_4$ followed by adsorption to Protein A-Sepharose and elution with 0.1 M glycine-HCl, pH 3.0. After adjusting the pH to 7.0 with 0.5 M $Na_2CO_3$, the volume of the solution was brought to the original volume of the antiserum used for the isolation. A 1:25 dilution of this purified IgG in 0.05 M Veronal buffer, pH 8.5 at 35°–40° C. was mixed with an equal volume of 2% agarose in the same buffer at 75° C. Of this mixture, 8.5 ml were applied to a 5×7.5 cm glass slide (previously coated with 0.3% agarose and dried), kept in a moist chamber at 4° C. and allowed to gel. Wells (1.3 mm) were punched in the agarose and samples of product from each purification step (approximately 3 μl) were added in duplicate. Serial dilutions of a lung tumor extract, LT-37, were used as standards and a unit was arbitrarily defined as the amount of antigen required to produce a circular precipitin ring of 2.7 mm in diameter. The plates were incubated under light paraffin oil for 42 h at 37° C., rinsed and washed overnight in PBS. The gel surface was covered with filter paper, dried at 37° C., stained 10–15 min with 0.1% Amido Black and then destained with 5% acetic acid until a clear background was obtained. The diameters of the precipitin rings were measured and the calculated areas were plotted against the concentration of standard as shown in FIG. 3. The assay was linear over a range of 1–30 units.

4. *Antichymotrypsin Assay*—A radial immunodiffusion assay, similar to the RID assay for hLTAA, was performed according to Princler, et al., *Quantitative Assay for α-1-antichymotrypsin by Radial Diffusion*, in Conference on Serologic Analysis of Solid Tumor Antigens, pp. 709–710, (S. Rosenberg, ed.), NY Academic Press, 1980. This assay has a range of 5–200 μg of ACT. The assay was included owing to observed competition between a previously reported antigen, hLTAA-2b, and serum $α_1$-antichymotrypsin in double antibody radioimmunoassays.

5. *Double Diffusion Analysis in Agarose*—Ouchterlony double diffusion analysis was performed in 1% agarose gel for 24–48 h at 20° C. as previously described by Braatz, et al., J. Natl. Cancer Inst., 61:1035, supra.

6. *DEAE-Cellulose Chromatography*—A column of DE-52, 350 ml bed volume, was equilibrated with 5 mM Tris-HCl, pH 8.1 (buffer A) at 4° C. until the effluent had the same conductance as the starting buffer. The crude extract was dialyzed against buffer A containing 0.5 mM phenylmethylsulfonly fluoride and 0.02% NaN$_3$, and then loaded onto the column which was washed with buffer A until the absorbance of the effluent at 280 nm was less than 0.07. A linear NaCl gradient from 0 to 0.2 M, with a total volume of 4 liters, was applied to the column, followed by a 1 M NaCl wash. All NaCl solutions were prepared in buffer A. Portions of fractions were concentrated using a Minicon Type B15 concentrator (Amicon Corp., Lexington, Mass.) and tested for LTAA or ACT content. Fractions eluting with the NaCl gradient that contained antigenic activity were pooled as indicated and then concentrated by ultrafiltration with an Amicon concentrator and a UM-20 membrane (Amicon Corp., Lexington, Mass.) to a final volume of 35 ml.

7. *Gel Filtration*—A column of Sephadex G-200, 3.5×143 cm, was equilibrated with 50 mM Tris-HCl, pH 8.1 at a flow rate of 15 ml/h. The column was calibrated with blue dextran and chymotrypsinogen-A (Sigma Chem. Co., St. Louis, Mo.), bovine serum albumin (Miles Laboratories Inc., Elkhart, Ind.), and NaN$_3$.

8. *Affinity Chromatography*—The IgG fraction from rabbit antiserum R-152 (25.8 mg, prepared as described under hLTAA assay, B-3, supra) was coupled to CNBr-Sepharose (35 cc gel) using the manufacturer's recommended procedure. Pooled fractions of antigenic activity from the G-200 profile were passed through the affinity column at 4° C. The column was washed with the equilibrating buffer, 0.01 M Tris-HCl, pH 8.1, containing 0.5 M NaCl and then eluted with 2.5 M NH$_4$SCN, pH 8.0. Fractions which eluted with thiocyanate were immediately pooled, dialyzed against the equilibrating buffer and stored at 20° C.

9. *Gel Electrophoresis*—Analytical polyacrylamide gel electrophoresis was performed according to Davis (*Discelectrophoresis, II. Method and Application to Human Serum Proteins*, Ann. NY Acad. Scie., 121:404–427, 1964), without stacking gels. Staining for protein was performed using Coomassie Brilliant Blue G-250 as detailed in Braatz, et al., J. Natl. Cancer Inst., 61:1035, supra. For the determination of antigenic activity in the gel after electrophoresis, 2.5 mm slices were placed in agarose wells of the same diameter and double diffusion analysis against rabbit antiserum R-201 was performed.

10. *Analytical-Procedures*—Protein was determined with the Bio-Rad protein assay reagent, using bovine serum albumin as standard, according to Bradford, M.M., *A Rapid and SensiMethod for the Quantitation of Microgram Quantities of Protein Utilizing the Principle of Protein Dye-Binding*, Anal. Biochem., 72:248–254, 1976.

C. Discussion of Results

Figure 4:
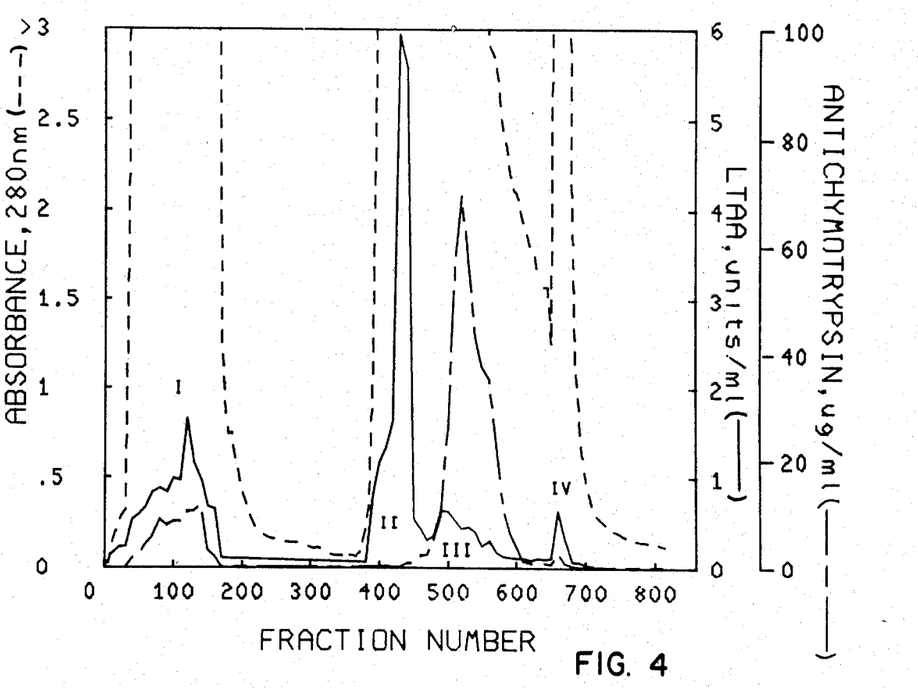
FIG. 4 is a graphic representation of DEAE-cellulose chromatography of crude LT-120 extract. Tumor antigen activity was measured by radial diffusion assay. Antichymotrypsin activity was also determined with a radial diffusion assay. Absorbance at 280 nm and the conductance of the effluent were also determined. The NaCl gradient (0–0.2 M) ran from fraction number 355 to 635 and was linear as determined by conductivity measurements. One molar NaCl was applied at the end of the gradient. Pools of fractions were collected as follows: pool I, 11–175; pool II, 375–469; pool III, 471–575; pool IV, 651–669.
Figure 5:
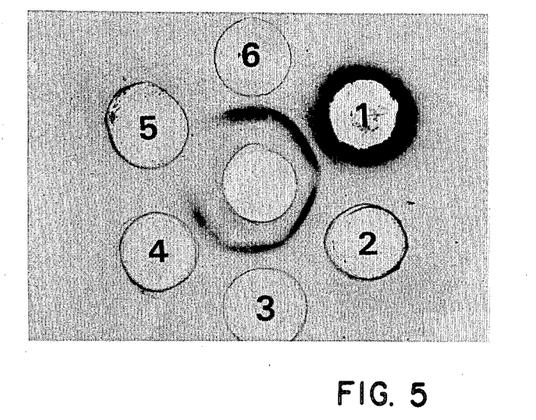
FIG. 5 is a photographic representation of the results of Ouchterlony double diffusion analysis of DEAE-purified antigens, of FIG. 4. Center well, adsorbed immune serum R-152; 1, pool I; 2, pool II; 3 and 6, LT-37; 4, pool III; 5, pool IV. The minor reactivities seen with wells 1, 4, and 5 are residual normal reactivities due to incomplete adsorption and are not related to the major tumor antigenic component.

The crude extract from tumor tissue (ca. 2 liters) was subjected to DEAE-cellulose chromatography. The elution profile indicated multiple peaks of antigenic reactivity (FIG. 4). Three major regions containing antigenic activity are referred to as peaks I, II and III in their order of elution. A negligible amount of activity, peak IV, eluted with 1 M NaCl. The predominant component, peak II, eluted soon after the application of the gradient, at about 0.045 M NaCl, and contained more than four (4) times as much antigen as peak III which eluted at about 0.08 M NaCl. Peak I contained almost one-fourth as much activity as peak II but did not result from overloading the column: when it was reapplied to a fresh column of DEAE-cellulose three-fourths of the antigenic activity was again recovered in the unbound fractions. Despite the fractionation of antigenic activity into multiple components, the antigens in peaks I, II and III were observed to give precipitin lines of identity by double diffusion analysis (FIG. 5). In addition, each of the three (3) components produced lines of identity with the standard lung tumor extract, LT-37, which itself is representative of most lung tumor extracts which have been treated in this fashion. Therefore, these components appeared to have identical antigenic sites, which were also common to human lung cancers in general.

The quantitative aspects of this and the subsequent purification steps are presented in Table I below. The sum of the activity present in the four (4) peaks represents 75% of the activity applied to the column, while peak II alone accounted for 49% of the activity.

Figure 6:
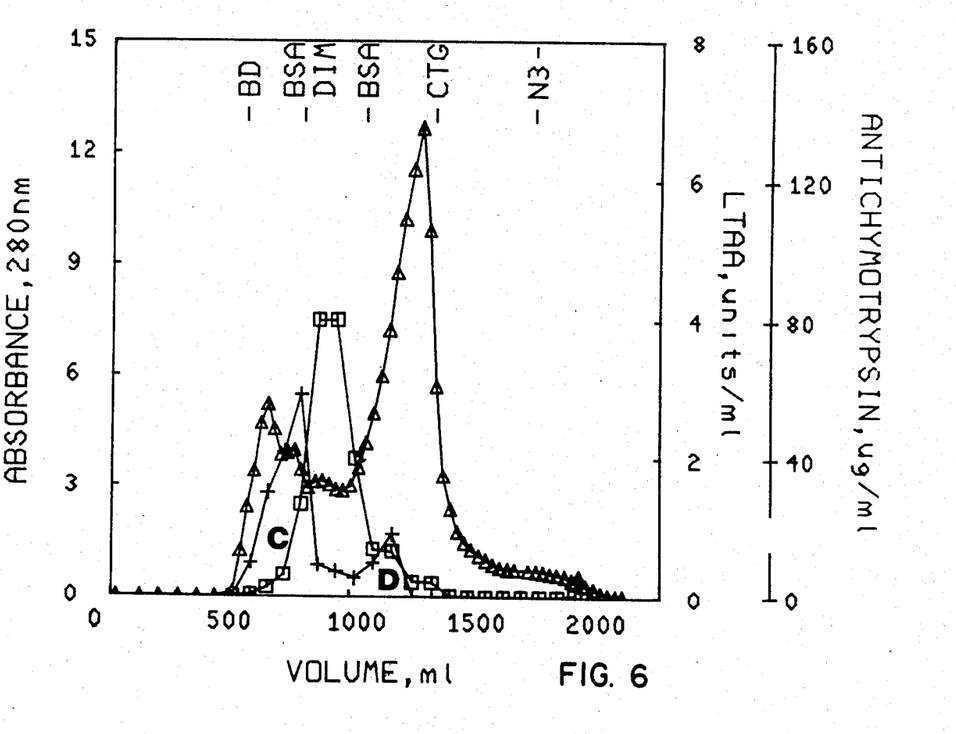
FIG. 6 is a graphic representation of G-200 chromatography of DEAE pool III, of FIG. 4. Fractions were tested for absorbance at 280 nm (Δ—Δ), hLTAA (+—+) and antichymotrypsin (□—□) activity by radial immunodiffusion. Two pools of activity were collected, pool C, 549–905 ml and pool D, 913–1171 ml. Standards are as indicated in FIG. 7.

Fractions were also assayed for $\alpha_1$-antichymotrypsin (ACT) for comparison with a previously isolated lung tumor antigen, hLTAA-2b, which is immunochemically related to ACT. As shown in FIG. 6, peak II was clearly separated from ACT and thus by this analysis was distinct from lung antigen hLTAA-2b. Peak III showed some overlap with ACT; however, the two (2) peaks appeared distinct. Based on additional evidence to be presented below, it was concluded that they are unrelated.

Figure 7:
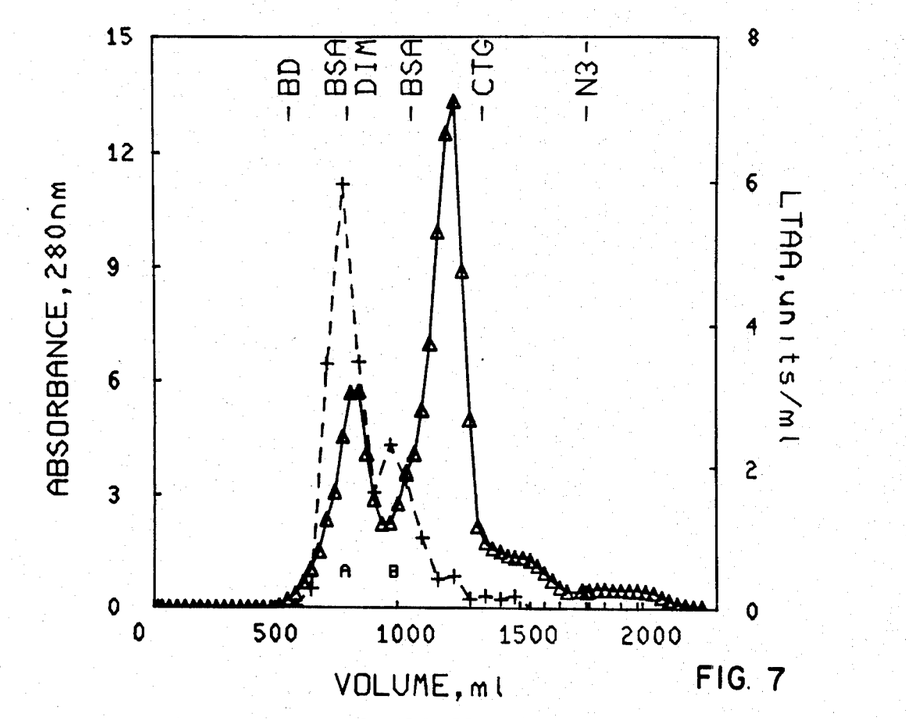
FIG. 7 is a graphic representation of G-200 chromatography of DEAE pool II of FIG. 4. Fractions were tested for absorbance at 280 nm (Δ—Δ) and hLTAA content by the radial diffusion assay (+—+). Standards indicated are: BD, blue dextran; BSA DIM, dimer of bovine serum albumin; BSA, bovine serum albumin; CTG, chymotrypsinogen; $N_3-$, sodium azide. Two pools of activity were collected as follows: pool A, 654–900 ml and pool B, 913–1095 ml.
Figure 8:
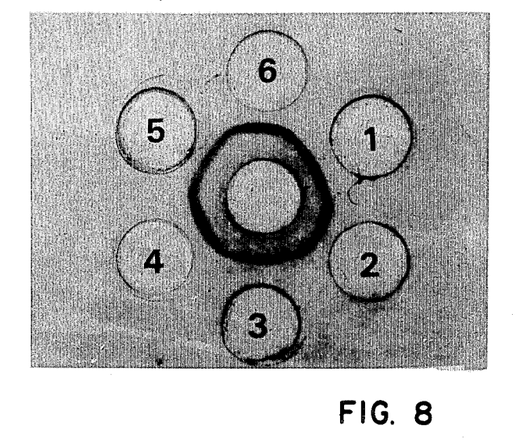
FIG. 8 is a photographic representation of the results of Ouchterlony double diffusion analysis of G-200 purified antigens of FIGS. 6 and 7. Center well, adsorbed immune serum R-201; 2, 4, and 6, LT-37; 1, pool A (from FIG. 7); 3, pool B (from FIG. 7); 5, pool C (from FIG. 6).

Concentration of peak II by ultrafiltration followed by Sephadex G-200 chromatography resolved the antigenic activity into two (2) additional components (FIG. 7). The major peak eluated at a $V_e/V_o$ of 1.4, corresponding to globular proteins of $M_r=135,000-150,000$. Approximately 41% of the applied activity was contained in this pool of fractions, whereas the minor peak eluted at $V_e/V_o$ of 1.75 and contained about 10% of the applied activity. The major peak may represent a more polymerized form of the minor peak, since the latter eluted in a region containing globular proteins of approximately 80,000 daltons, roughly one-half the size of the major component. The two (2) forms were immunochemically related, giving a precipitin line of identity in Ouchterlony double diffusion (FIG. 8). Each peak was further purified by affinity immunoadsorption chromatography.

The IgG fraction isolated from the rabbit immune serum (R-152) was coupled to Sepharose 4B and used as the affinity matrix. Each one of the two G-200 pools containing antigenic activity was applied to the column and separated into two (2) fractions: the unbound fraction which was eluted with Tris buffer (0.01 M, pH 8.1, containing 0.5 M NaCl) and the bound fraction which eluted with 2.5 M NH$_4$SCN, pH 8.0. The latter fraction was immediately dialyzed vs Tris buffer to remove NH$_4$SCN and stored at −20° C. The unbound fraction was recycled through the column twice in order to remove all antigenic activity. The total antigenic activity recovered after the three (3) cycles of binding and elution represented about 67% of the activity first applied to the column (Table I).

Figure 9:
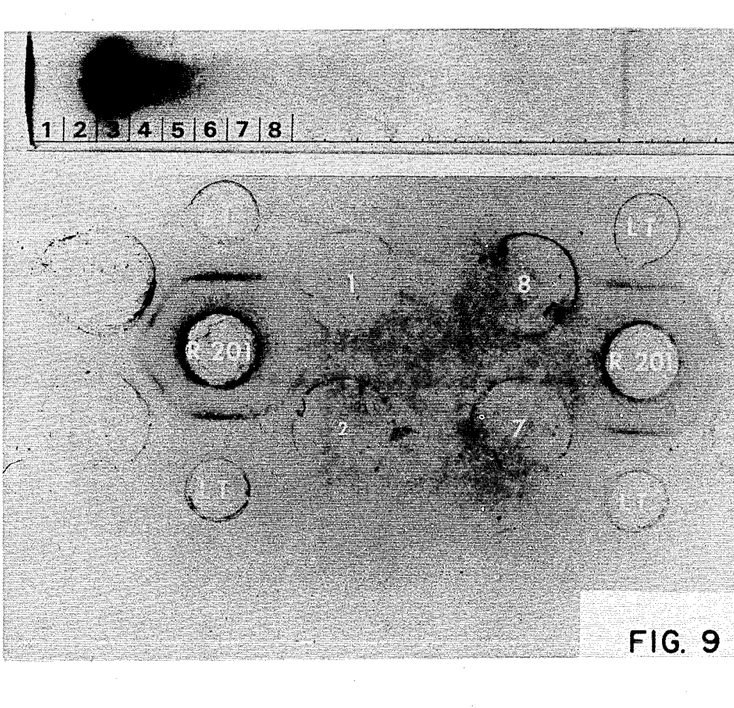
FIG. 9 is a photographic representation of the results of polyacrylamide gel electrophoresis of affinity-purified hLTAA and detection of antigenic activity. Two 7% polyacrylamide gels, each containing 27 μg protein were electrophoresed, one was sliced in 2.5 mm sections and the other stained with Coomassie Blue. Each slice was placed in an appropriate size well and the protein allowed to diffuse against R-201 (center well). Upper and lower wells (unlabelled) in each pattern contained LT-37 for comparison. Slices 9–24 were all negative for antigen.

Polyacrylamide gel electrophoretic analysis of the fraction which bound to and was eluted from the antibody column demonstrated the degree of purity of this material. FIG. 9 shows a representative pattern obtained when the affinity-purified preparation was electrophoresed on a 7% acrylamide gel. One major protein staining component was evidence, with some diffuse anodal staining. For the purpose of locating the antigenic reactivity, an identical gel with the same protein load (27 μg) was electrophoresed at the same time. The tracking dye migrated to the same position in both gels, 50 mm. Slices (2.5 mm) of the unstained gel were tested for immunoprecipitable activity by Ouchterlony analysis using the rabbit immune serum R-201. The antigenic activity corresponded closely to the major staining component, with $R_f$ ranges of 0.09–0.22 and 0.11–0.17, respectively. Electrophoresis in 5% acrylamide gels gave a similar result, with the protein and activity showing increased, but identical mobilities.

The primary antigen described here is the affinity-purified, first G-200 peak (peak A) which in turn was obtained from DEAE-peak II. In addition to this, peak III from DEAE was also chromatographed on Sephadex G-200. The antigenic profile obtained (FIG. 6) was similar to the profile obtained with peak II (FIG. 7), again showing two (2) peaks of antigenic activity (peaks C and D). It appears that these various forms are immunochemically related size and/or charge isomers.

Figure 10:
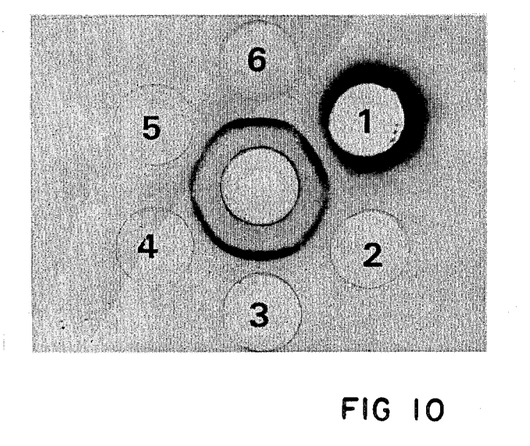
FIG. 10 is a photographic representation of the results of Ouchterlony double diffusion analysis of affinity-purified hLTAA. Center well, adsorbed immune serum R-201; 1, crude extract; 2, affinity pool 1; 3 and 6, LT-27; 4, affinity pool 2; 5, affinity pool 3.

Affinity immunoadsorption was also performed on peak B (FIG. 7) and peak C (FIG. 6). When these pools of affinity-purified antigens (affinity pools 2 and 3, respectively) along with the first affinity-isolated antigen (affinity pool 1) were tested in double diffusion, lines of identity resulted not only among each other, but also with the antigen present in a standard extract, LT-37 (FIG. 10), indicating the common nature of these antigens. Lines of identity between the purified and crude forms of the antigens were also demonstrated (wells 1 and 2), suggesting that the antigen was isolated intact.

II. Characterization of hLTAA and Development of Radioimmunoassay

A. Materials

Proteins used to standardize size exclusion columns were: aldolase, bovine serum albumin, chymotrypsinogen-A and cytochrome c, from Pierce Chemical Co., and apoferritin and IgG from Schwarz, Mann. *Escherichia coli* alkaline phosphatase and bovine pancreatic α-chymotrypsin were from the Sigma Chemical Co. Antisera to $\alpha_1$-antichymotrypsin was obtained from Dako, distributed by Accurate Chemical and Scientific Corp., Hicksville, NY. Pansorbin and Sansorbin (Protein A-containing and deficient forms of inactivated *Staphylococcus aureus*, respectively) were purchased from Calibiochem-Behring Corp., Bolton-Hunter reagent, 4000 Ci/mmol, was obtained as soon as possible after preparation from New England Nuclear. Lung cancer sera (kindly supplied by Dr. J. Concannon, Allegheny General Hospital, Pittsburgh, PA) were pretreatment specimens from newly diagnosed patients with lung cancer of various histologic types. Normal sera were obtained from the National Institutes of Health Clinical Center Blood Bank.

B. Methods

1. *Radioiodination*—Partially purified lung tumor-associated antigen (pool 1 from the affinity immunoadsorption separation described I-B-8, supra) was radioiodinated by the procedure of Bolton and Hunter (*The Labelling of Proteins to High Specific Activities by Conjunction to an $^{125}I$-containing Acylating Agent*, Biochem. J., 133:529–538, 1973). Ten micrograms of protein in 100 μl of 0.1 M sodium borate, pH 8.6 was added to 1 mCi N-succinimidyl-3-(4-hydroxy-5-[$^{125}I$] iodophenyl) propionate (Bolton-Hunter reagent) after careful removal of benzene from the latter with a gentle stream of $N_2$. After 20 min at 0° C., 0.5 ml of 0.5 M glycine was added for an additional 5 min and the mixture was chromatographed over a PD-10 column (Pharmacia), previously equilibrated with $PBS^2$ containing 30% glycerol. Routinely, the void volume of the column was collected and further purified by preparative gel electrophoresis as described below.

2. *Gel Electrophoresis*—Analytical polyacrylamide gel electrophoresis was performed according to Davis and stained with Coomassie Blue G-250 as previously described in Braatz, et al., J. Natl. Cancer Inst., 61:1035, supra. SDS gel electrophoresis was conducted according to Weber and Osborn, *The Reliability of Molecular Weight Determinations by Dodecyl Sulfate-Polyarcylamide Gel Electrophoresis*, J. Biol. Chem., 244:4406–4412, 1969, and stained as in Braatz, et al., J. Natl. Cancer Inst., 61:1035, supra.

For the preparative isolation of radioiodinated antigen, 1 ml of the void volume from the PD-10 column was loaded onto standard 7% gels (1×11 cm) and electrophoresed at 4° C. for an additional 2 h after the tracking dye eluted from the gel. This allowed better resolution of the two (2) slower moving components that were of interest. The gels were then sliced into 5 mm sections and the slices containing radiolabelled antigen were re-electrophoresed in order to extract the labelled proteins, according to Braatz, et al., *A Rapid and Efficient Method for the Isolation of Proteins from Polyacrylamide Gels*, Prep. Biochem., 7:495–509, 1977. Recoveries of iodinated antigen were generally in the 50–70% range.

3. *Gel Filtration*—Analytical Sephadex G-200 chromatography was performed at 4° C. on a 1.2×94 cm column equilibrated with 0.05 M Tris HCl, pH 8.1 containing 0.1 M NaCl at a flow rate of 4.1 ml $cm^{-2}h^{-1}$. Fractions (0.86 ml) were collected and protein was determined by absorbance at 280 nm, or 410 nm for cytochrome c. Radioactivity was determined with a BioGamma counter (Beckman Instruments, Inc.). The standards used and their elution volumes were: blue dextran, 32.7 ml; apoferritin, 33.5 ml; aldolase, 44.7 ml; BSA dimer, 43.0 ml; BSA monomer, 53.8 ml; chymotrypsinogen-A, 67.1 ml; and cytochrome c, 73.5 ml.

The $D_{20,w}$ for the antigen was calculated using these data and the known diffusion coefficients for each standard by constructing a plot of $1/D_{20,w}$ versus the elution volume/void volume ratio. (Ackers, *Molecular Exclusion and Restricted Diffusion Processes in Molecular Sieve Chromatography*, Biochemistry, 3:723–730, 1964; Andrews, *The Gel Filtration Behavior of Proteins Related to their Molecular Weights Over a Wide Range*, Biochem. J., 96:595–605, 1965; DeVincenzi, et al., *Reevaluation of the Molecular Weights of Glycogen Phosphorylases A and B Using Sephadex Gel Filtration*, Biochemistry, 6:348–3497, 1967.) Linear regression analysis of these data was performed using the curve fitting procedures of the MLAB program on the National Institutes of Health DEC-System 10 computer.

4. *High Performance Liquid Chromatography*—The apparatus used was a Model 334 MP Liquid Chromatograph system with a Model 155-40 variable wavelength detector (Beckman/Altex). A Spherogel TSK-3000 SW column and precolumn (Altex) were used in conjunction with a 20 μl loop at a flow rate of 0.7 ml $min^{-1}$ with 0.05 M sodium phosphate, pH 7.0 containing 0.3 M NaCl as the mobile phase. Effluent absorbance was monitored at 210 nm for greater sensitivity. All buffers and standard protein solutions were prepared in glass distilled water and filtered through a 0.22 μm filter (Nalgene). The data were analyzed and the diffusion coefficient calculated as described above. The standards and their elution volumes were: blue dextran, 10.2 ml; apoferritin, 11.0 ml; IqG, 13.3 ml; BSA dimer, 14.8 ml; BSA monomer, 17.2 ml; chymotrypsinogen-A, 21.8 ml; and cytochrome c, 22.6 ml.

5. *Sedimentation Velocity Analysis*—The $S_{20,w}$ value for the hLTAA was determined by the method of Martin and Ames (A Method for Determining the Sedimentation Behavior of Enzymes, J. Biol. Chem., 236:1372–1379, 1961), as previously described in Braatz, et al., J. Natl. Cancer Inst., 61:1035, supra, using *E. coli* alkaline phosphatase, $S_{20,w}=6.2$ S and bovine pancreatic α-chymotrypsin, 2.56 S as standards (Garen, *A Fine Structure Genetic and Chemical Study of the Enzyme Alkaline Phosphatase of E. coli, I. Purification and Characterization of Alkaline Phosphatase*, Biochem. Biophys. Acta., 38:470–483, 1969; Schlesinger, *The reversible Dissociation of the Alkaline Phosphatase of E. coli*, J. Biol. Chem., 240:4284–4292, 1965; and Smith, *Sedimentation Behavior of Derivatives of α-chymotrypsin*, J. Biol. Chem., 195:525–530, 1952).

6. *Isoelectric Focusing*—The apparatus used consisted of a 110 ml LKB 8100 Ampholine Electrofocusing Column (LKB Instruments, Inc., Rockville, MD) and Isco Model 494 Electrophoresis Power Supply (Instruments Specialties Company, Lincoln, Neb.). A linear gradient of glycerol (5–50% prepared in freshly deionized water, 50 ml of each), containing 1% (final concentration) carrier ampholytes, was formed in the column with an Ampholine Gradient Mixer (LKB). Half of the following mixture of ampholytes was added to each solution forming the glycerol gradient: 1 ml pH 3.5–5, 2.5 ml pH 4–6, and 5 ml pH 2.5–4 LKB 1809 Ampholine carrier ampholytes. Purified and radioiodinated hLTAA was mixed with the high density glycerol solution and introduced into the column after approximately half the gradient had been formed. The anolyte was 1 M acetic acid in 50% glycerol and the catholyte was 2% LKB 1809 Ampholine, pH 6–8 in 5% glycerol. Focusing was carried out for 27 h at 4° C., at a constant power of 15 W, during which the voltage rose from 1000 to 1550 V and the current dropped from 15 to 9.9 mA. After focusing, the solution was pumped from the column and 0.5 ml fractions were collected and subjected to pH and radio-activity measurements.

7. *Immunoassays*—Binding of radioiodinated hLTAA to R-201 was performed in 400 μl polyethylene Microfuge tubes. Twenty-five (25) microliters of labelled antigen containing 15,000–20,000 cpm was mixed with 10–200 μl of a 1:2000 dilution of R-201 in a total volume of 350 μl. Dilutions and volume adjustments were made with PBS containing BSA at 1 mg/ml. After 16 h at 4° C., 30 μl of a 50% suspension of Pansorbin was added and incubated for an additional 1.5 h. The suspension was centrifuged for 1 min in a Beckman Microfuge and the supernatant was aspirated. The tip containing the pellet was removed with a razor and radioactivity was determined in a gamma counter. Incubations with Pansorbin from 1–5 h gave similar results. Binding with the Sansorbin control was insignificant.

For the generation of the standard binding inhibition curve (FIG. 11) and the analysis of test sera (FIG. 12), a similar protocol was used but the total incubation volume was 1.0 ml and R-201 was used at a constant final dilution of 1:15,000. The antigen preparation used as the inhibitor was pool 1 from the affinity immunoadsorption described in I-C, supra. The pellet was sedimented for 10 min at 3000×g, the supernatant drained and the pellet counted in a gamma counter. The logit-log transformation of the binding data was used for analysis of the results according to Rodbard, et al., *Rapid Calculation of Radioimmunoassay Results*, J. Lab. and Clin. Med., 74:770–781, 1969. Sera from normal or lung cancer paitents were assayed for hLTAA by including 10 μl of sera during the first incubation and the amount of binding was used to determine, from the standard binding inhibition curve, their concentration of hLTAA.

8. *Other Procedures*—*E. coli* alkaline phosphatase and chymotrypsin activities were deterimed using p-nitrophenylphosphate (Braatz, et al., J. Natl. Cancer Inst., 61:1035, supra) and benzoly-L-tyrosine ethyl ester (Hummel, *A Modified Spectrophotometric Determination of Chymotrypsin, Trypsin, and Thrombin*, Can. J. Biochem. Physiol., 37:1393–1399, 1059).

C. Discussion of Results

Figure 13:
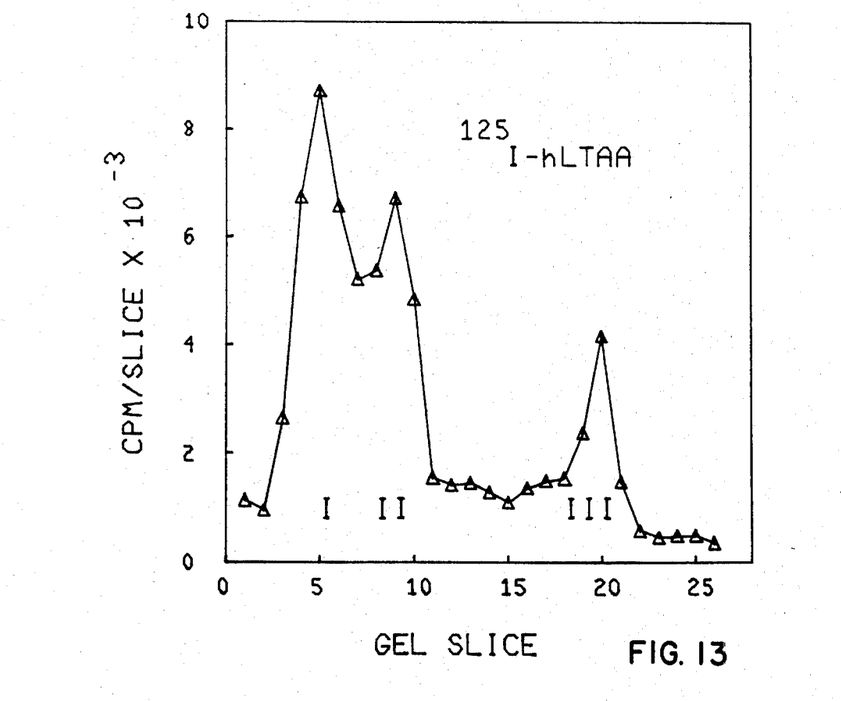
FIG. 13 is a graphic representation of the gel electrophoresis of radioiodinated antigen (of FIG. 1) for 1 h after the tracking dye ran off the bottom. This resulted in separation of the major peak into two components (I and II) and better separation of these from the unreactive protein (peak III).
Figure 14:
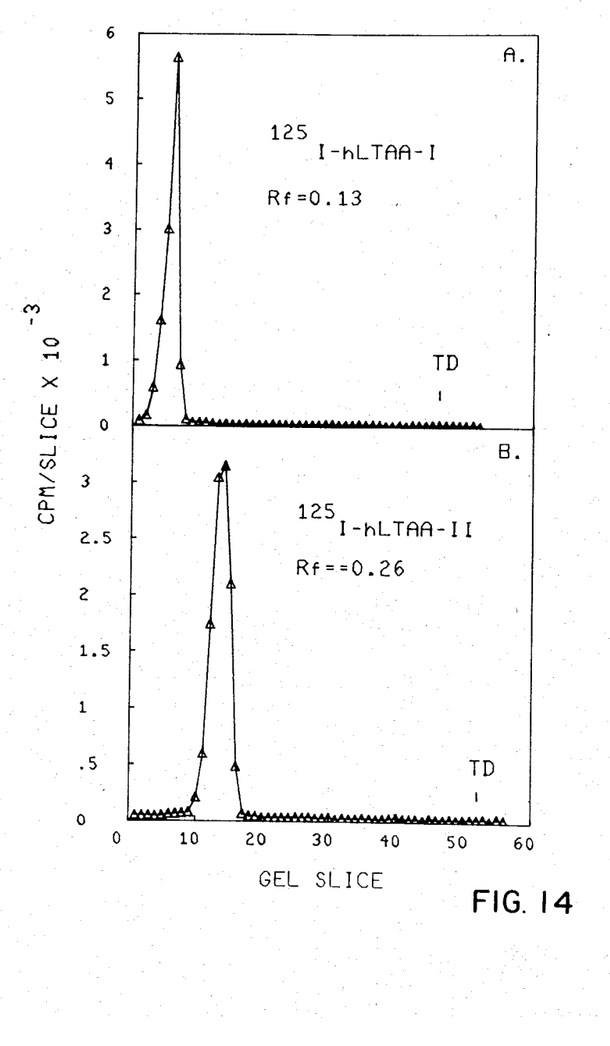
FIG. 14 is a graphic representation of the polyacrylamide gel electrophoresis of isolated peaks I and II from FIG. 13. The $R_f$ values were calculated relative to the dye front.

1. *Radioiodination of hLTAA*—Attempts at labelling the partially purified LTAA with $^{125}$Iodine by the chloramine T method of Hunter and Greenwood (*Preparation of Iodine-131 labelled Human Growth Hormone of High Specific Activity*, Nature, 194:495–496, 1962) were unsuccessful, with negligible incorporation of radioactivity into material with an $R_f$ of 0.0—0.2 on 7% polyacrylamide gels. This failure to incorporate radioactive iodine into the protein was not corrected by treatment of the protein with SDS prior to radioiodination, which would expose potentially buried tyrosine groups. For this reason all subsequent radioiodinations were performed with Bolton-Hunter reagent, which yielded levels of incorportion of $^{125}$I into protein of from 0.1–2.0 μCi/μg. Electrophoresis of this radioiodinated purified antigen on 7% polyacrylamide gels indicated the presence of two (2) components with $R_f$ values of 0.15 and 0.44 (FIG. 1, panel A). Since gel electrophoresis of the unlabelled antigen produced only one (1) component which stained with Coomassie Blue and which had an $R_f$ comparable to the slower moving component in FIG. 1, panel A, it was of interest to determine whether both of the radiolabelled peaks reacted with immune serum. FIG. 1, panel B, shows the effect of immune serum on these components. The slower peak was totally excluded by the gel as expected for immune complexes, whereas the mobility of the faster peak was unchanged. In a separate experiment, the labelled components were isolated from the gel after electrophoresis and mixed with immune serum, R-201. Radiolabelled antigen which bound to antibody was separated from the free from by Pansorbin as described in II-B-7, supra. With a dilution of antiserum which produced 30% precipitation of the slow peak, only 3% of the faster peak could be precipitated. Thus, the $R_f=0.44$ component appeared to be a non-antigenic contaminant or denatured antigen and was removed from the labelled mixture by preparative polyacrylamide gel electrophoresis. When electrophoresis was carried out for extended periods of time (generally for 1 h after the tracking dye ran off the gel) the reactive component could be resolved in two (2) peaks, as shown in FIG. 13. Even better resolution could be obtained in longer runs which eluted the fast, unreactive component from the gel. Using these conditions, both components of the reactive peak-designated (hLTAA-I and hLTAA-II) were isolated and shown by re-electrophoresis to be distinct (FIG. 14). Furthermore, analytical gel electrophoresis of a mixture of hLTAA-I and hLTAA-II resulted in complete separation of the two (2) components (data not shown). Radiolabelled hLTAA-I and hLTAA-II were added back to the unlabelled sample from which they were derived, and their positions in acrylamide gels used to locate unlabelled hLTAA-I and -II. Using this technique, 20-50 μg have been isolated of each for further studies (see results with HPLC, II-C-3, infra).

2. *Immunoreactivity of Iodinated hLTAA Forms I and II*—Although the results shown in FIG. 1 suggested that both peaks I and II should react with R-201, it was necessary to directly examine this point. FIG. 2 shows that both peaks I and II bound appreciably above the controls to varying dilutions of R-201. The similar shapes of the curves suggest the similarity of the antigenic combining sites contained within each component. Also demonstrated in this chart is that neither hLTAA-I nor hLTAA-II reacted with a commercial antiserum to alpha-1-antichymotrypsin (ACT). This distinguishes these proteins from hLTAA-2b, another protein recognized by R-201 and R-152, which has been shown to be cross-reactive with plasma ACT.

Figure 15:
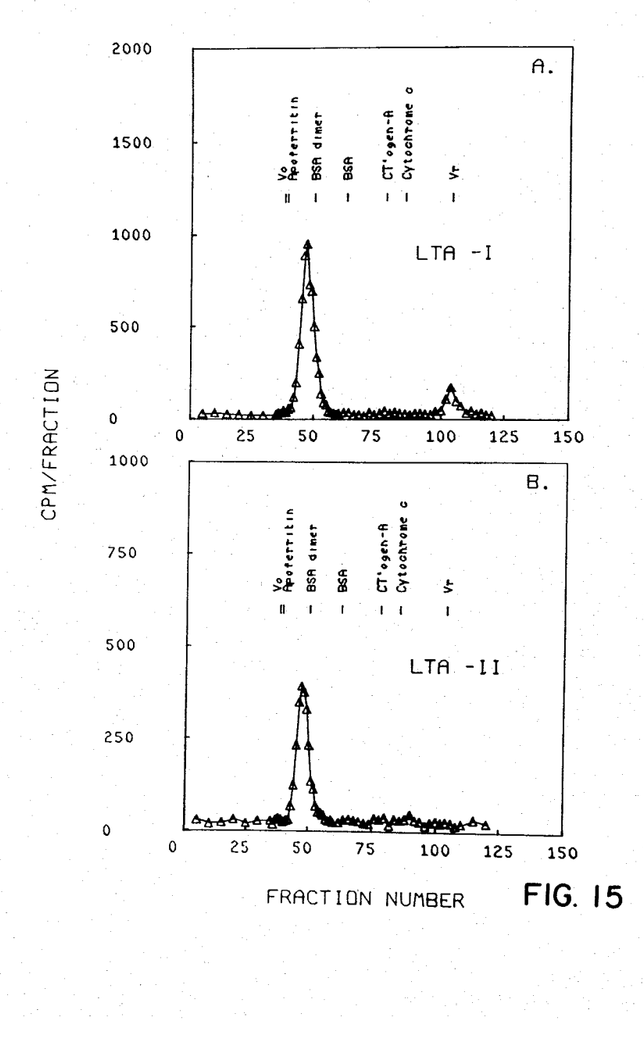
FIG. 15 is a graphic representation of the Sephadex G-200 chromatography of $^{125}$I-hLTAA-I (panel A) and $^{125}$I-hLTAA-II (panel B). The smaller peak at fraction number 104 in panel A represents free $^{125}$I. Standards are: blue dextran, $V_o$; apoferritin, $M_r = 480,000$; BSA dimer, $M_r = 134,000$; BSA monomer, $M_r = 67,000$; chymotrypsinogen-A, $M_r = 25,000$; and cytochrome c, $M_r = 12,500$.

3. *Biochemical Analysis of hLTAA-I and hLTAA-II*—Further characteriztion was then performed on both hLTAA-I and hLTAA-II. Gel filtration of each on an analytical column of Sephadex G-200 produced identical elution profiles, with both peaks eluting just prior to the dimer of BSA, indicating a molecular weight of approximately 140,000-150,000 (FIG. 15). The diffusion coefficient of the antigen was determined by comparing its elution position from Sephadex G-200 with that of a series of standards. A plot of the reciprocal of the diffusion coefficient of these standard proteins versus their elution positions ($V_e/V_o$) yielded a smooth curve, from which was interpolated a $D_{20,w}$ of $4.2 \times 10^{-7}$ cm$^2$s$^{-1}$ for the antigen.

Figure 16:
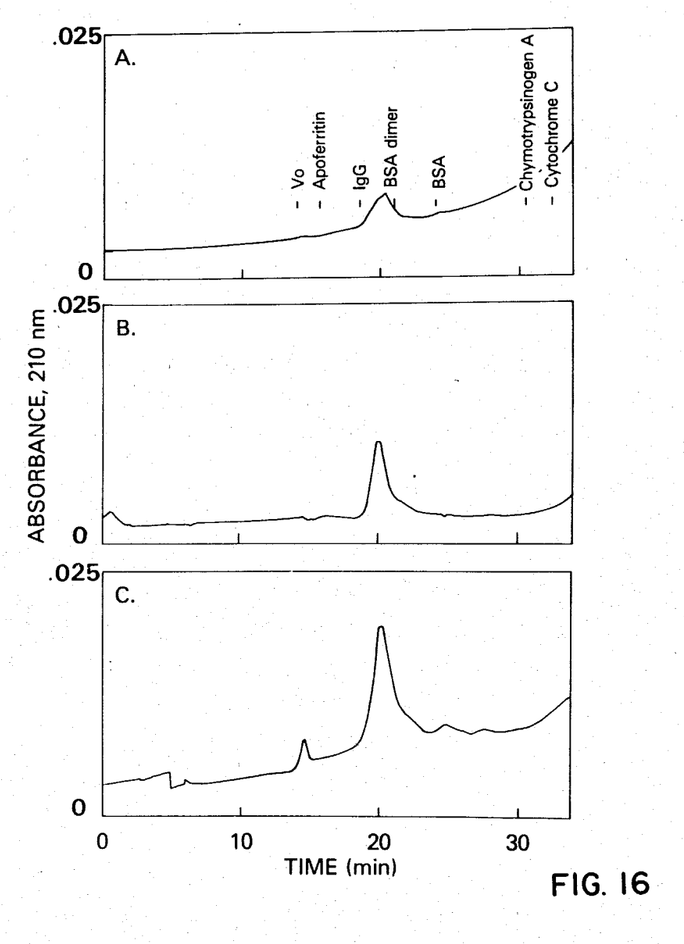
FIG. 16 is a graphic representation of the high performance liquid chromatography of unlabelled hLTAA-I (panel A) and hLTAA-II (panel B). A Spherogel TSK 3000 SW size exclusion column was used at a flow rate of 0.7 ml/min with 0.05 M sodium phosphate, pH 7.0, containing 0.3 M NaCl as the mobile phase. HPLC profiles of the pool 1 material from which hLTAA-I and hLTAA-II were isolated indicated the peak eluting at 20 min to be the major component, with minor components eluting at 14.5, 22 and 25 min (panel C). These contaminants were effectively removed by preparative gel electrophoresis since they are not detected in A and B.

High performance liquid chromatography (HPLC) was also performed on unlabelled hLTAA-I and hLTAA-II (isolated as described above). A Spherogel-TSK 3000SW (Altex) size exclusion column was used which yielded profiles similar to those obtained with Sephadex G-200 (FIG. 16). Again, both antigens eluted just prior to the elution of the dimer of BSA, with elution times of 20 min. Radiolabelled antigen eluted as a single, symmetrical peak with the same retention time of 20 min (data not shown). Panel C of FIG. 16 shows the HPLC chromatogram of the sample used for iodination in these studies, from which hLTAA-I and hLTAA-II were isolated. At least three (3) minor contaminants are detected which are removed by gel electrophoresis. As before with Sephadex, a series of standard proteins was chromatographed and a plot of 1/D vs $V_e/V_o$ constructed. From this curve, a value for the diffusion coefficient for the hLTAA was calculated to be $4.3 \times 10^{-7}$ cm$^2$s$^{-1}$, in close agreement with the value obtained using Sephadex G-200.

From the average of the diffusion coefficients obtained above, $4.25 \times 10^{-7}$ cm$^2$s$^{-1}$, we calculated the Stokes radius of the antigen to be 51 Å, according to Siegal, et al., in Biochem. Biophys. Acta., 112:246-362 (1966).

Figure 17:
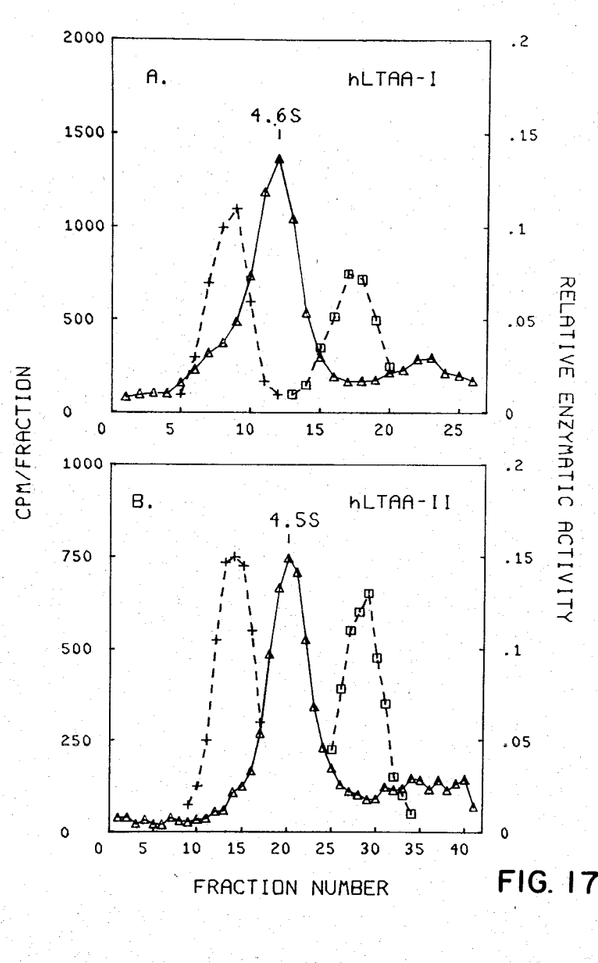
FIG. 17 is a graphic representation of the sucrose gradient sedimentation analysis of hLTAA-I (panel A) and hLTAA-II (panel B). Radiolabelled antigen (Δ—Δ) was compared to *E. coli* alkaline phosphatase (+---+) and α-chymotrypsin (□---□) as standards. Centrifugation was for 22 h at 5° C. at 149,632 ×g (average). Direction of sedimentation was from right to left.

Analysis of hLTAA-I and -II by velocity sedimentation in 5-20% sucrose gradients (FIG. 17), showed each to behave as a single sedimenting species. When compared with two (2) standard proteins, *E. coli* alkaline phosphatase (6.2 S) and bovine pancreatic α-chymotrypsin (2.56 S), hLTAA-I and -II were found to have indistinguishable sedimentation coefficients of 4.6±0.4 S and 4.5±0.2 S, respectively.

Figure 18:
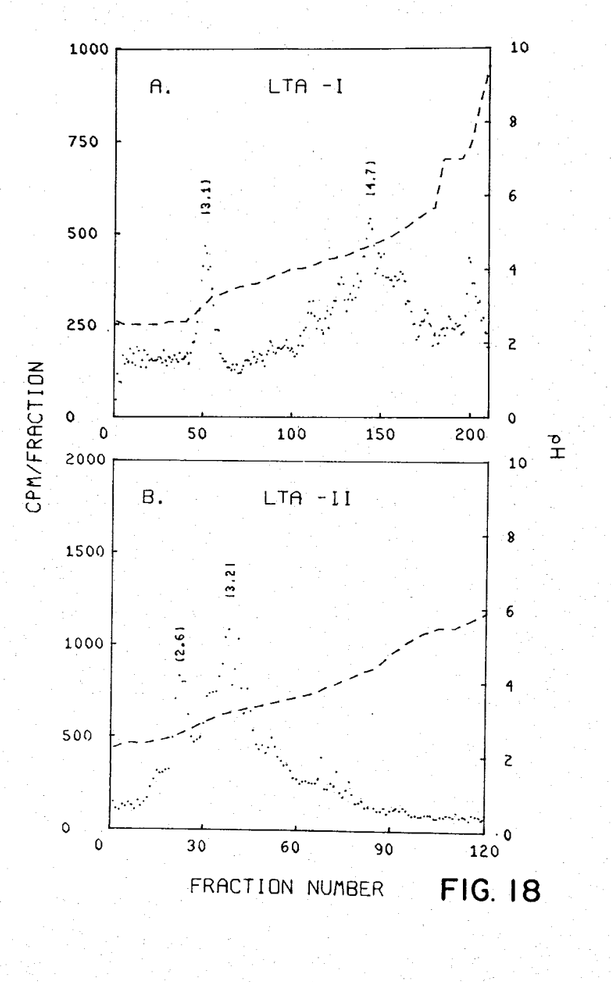
FIG. 18 is a graphic representation of the isoelectric focusing of hLTAA-I (panel A) and hLTAA-II (panel B). Samples were focused for 27 h at 4° C. in a 110 ml gradient of 5–50% glycerol. Each fraction was counted for $^{125}$I content and the pH was determined.

The ability to separate hLTAA-I and -II by acrylamide gel electrophoresis, despite their very similar size as evidenced by gel filtration and sedimentation velocity analysis, suggests then that they differ in charge. To address this point, isoelectric focusing was performed on each (FIG. 18). As expected from its greater electrophoretic mobility in acrylamide gels, peak II was shown to have a greater net negative charge. Peak II focused around pH 3.2 with a smaller component at pH 2.6, whereas hLTAA-I focused primarily around pH 4.7, with a minor component at pH 3.1.

Figure 19:
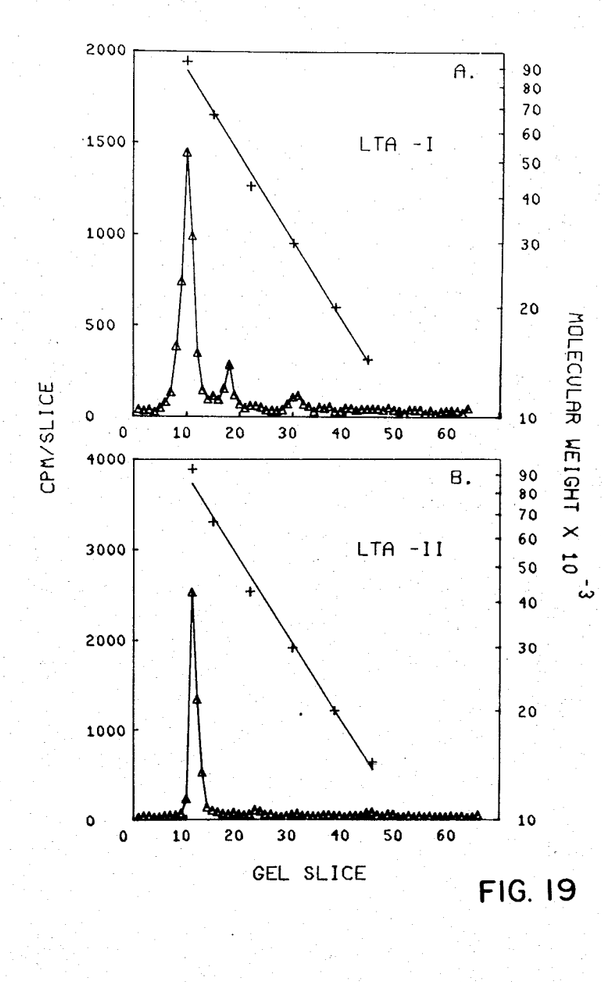
FIG. 19 is a graphic representation of the sodium dodecyl sulfate gel electrophersis of hLTAA-I (panel A) and hLTAA-II (panel B). Shown are results obtained with 7.5% acrylamide gels. Gels containing 10 and 12.5% acrylamide were also used and the standard curves obtained in each were subjected to linear regression analysis prior to estimation of the $M_r$ of the unknowns. The average value obtained is independent of acrylamide concentration. The standards used and their molecular weights were: phosphorylase b, 94,000; bovine serum albumin, 67,000; ovalbumin, 43,000; carbon anydrase, 30,000; soybean trypsin inhibitor, 20,100; and α-lactalbumin, 14,400.

Analysis by SDS gel electrophoresis consistently showed hLTAA-II to be a single component (FIG. 19). The pattern obtained was independent of the concentration of acrylamide, and the $M_r$ was calculated as 81,700, based on the average of values (89,000, 76,000 and 80,000) obtained using 7.5, 10.0 and 12.5% acrylamide gels, respectively. Peak I on the other hand was found to be composed of a major component, identical in size to peak II, and two (2) minor components of $M_r=50,000$ and 27,700. These results were likewise independent of acrylamide concentrations.

Figure 11:
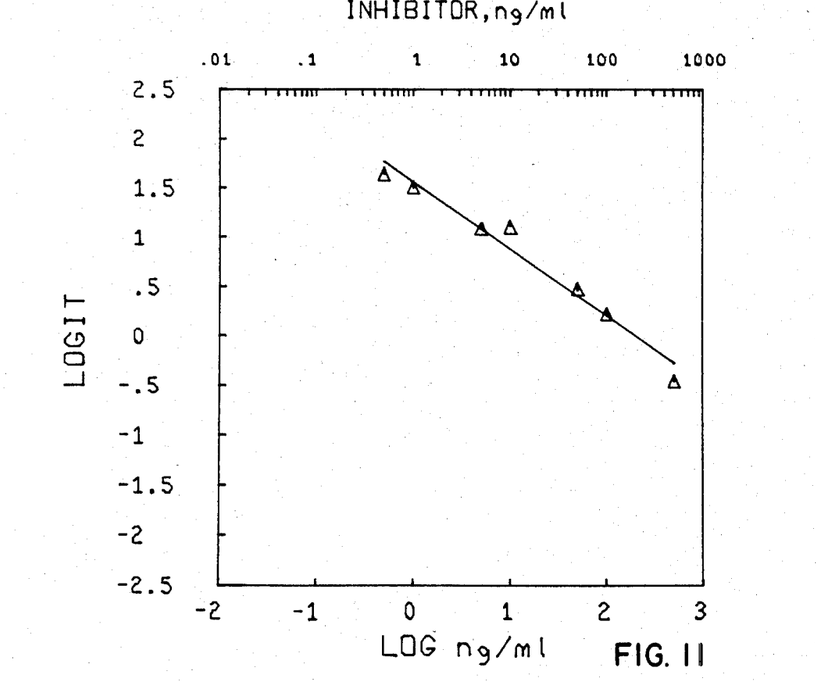
FIG. 11 is a standard binding inhibition curve for the hLTAA radioimmunoassay. Radiolabelled hLTAA-I was incubated 16 h at 4° C. with immune serum in the presence of varying amounts of unlabelled antigen. Antigen bound to antibody was separated using Pansorbin and quantitated as described in Methods.

4. *Development of a Radioimmunoassay*—The radioimmunoassay for quantitating the antigen in clinical specimens was developed using hLTAA-I as the trace-labelled antigen. Form hLTAA-I was selected on the basis of its greater availability. Subsequent experiments gave identical results using both forms. Labelled antigen was incubated overnight with antiserum at 4° C., and the bound and free antigen was separated by Pansorbin as described in II-B-7, supra. A standard binding inhibition curve was obtained, as shown in FIG. 11, by including known amounts of unlabelled antigen in the overnight incubation. The logit-log transformation of the binding data indicated a useful range of 1-100 ng/ml.

Figure 12:
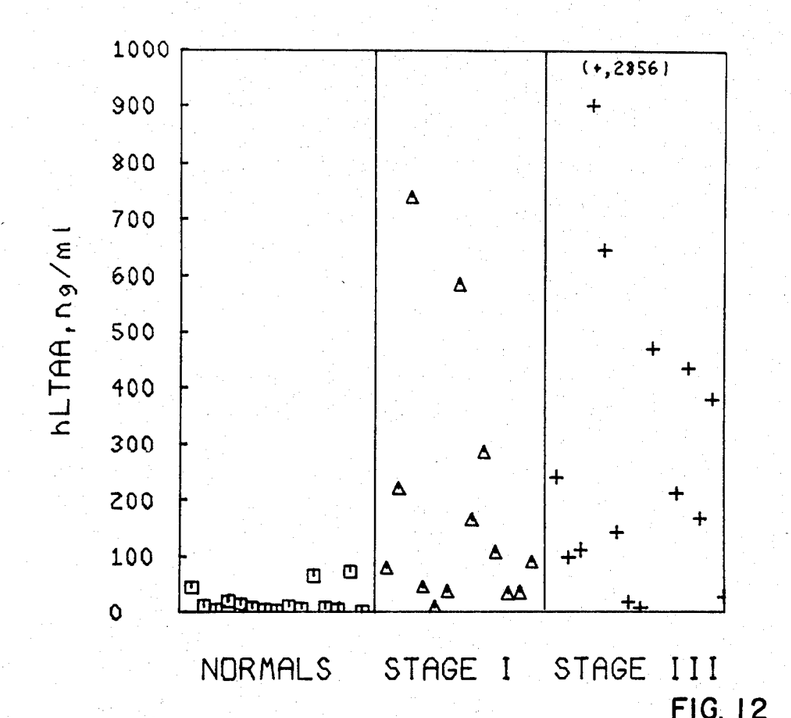
FIG. 12 is a graph of the quantitation of hLTAA in the serum of lung cancer patients versus normal individuals. Inhibition of binding of radiolabelled hLTAA to immune serum in the presence of test sera was converted to antigen concentration in the sera by interpolation from the standard curve (FIG. 11).

5. *Detection of hLTAA in Sera Of Lung Cancer Patients*—Three (3) groups of sera were tested: 15 from normal individuals, 13 from Stage I lung cancer patients, and 15 from Stage III lung cancer patients. The antigen concentration in each serum, obtained by interpolation from FIG. 11 of the amount of inhibition each produced in the binding assay, is shown in FIG. 12. With normal sera, there was a clustering of low values with a mean (±S.D.) of 17±22 ng/ml. Elevated and more divergent values were obtained with both Stage I and Stage III lung cancer sera. The means (±S.D.) for these groups were 187±219 and 277±252 ng/ml, respectively. By arbitrarily selecting a cutoff of 83 ng/ml, which is three (3) standard deviations above the means of normals, 7/13 Stage I sera, 12/15 Stage III sera and 0/15 normal sera exceeded this value. As predicted from the negative results with Ouchterlony double diffusion, all but one of the sera had hLTAA levels of less than 1 μg/ml. However, a large proportion of the lung cancer sera had levels of antigen that were clearly higher than those in normal sera. The ability to discriminate Stage I from Stage III disease is less certain, although the results suggest that later stages of the disease are associated with higher and more frequent elevations of circulating antigen.

6. *Clinical RIA Procedure for hLTAA*—To a series of 0.4 ml polyethylene microcentrifuge tubes were added 0.1 ml of a 1:320 dilution of normal rabbi serum.

1. To a set of four of these tubes the following were added, mixing well after each addition:
   a. 0.1 ml of radioiodinated hLTAA containing approximately 20000 cpm.
   b. sufficient PBS (0.01 M sodium phosphate, pH 7.4, 0.15 M sodium chloride) containing 1 mg/ml bovine serum albumin (BSA), such that the final volume if 1.0 ml. This set will gan an estimate of the non-specific binding (NSB).
2. To another set of four tubes were added the following, mixing well after each addition:
   a. 0.1 ml of a 1:1000 dilution of antiserum to hLTAA (R-201).
   b. same as in 1a and 1b. This set will give an estimate of the maximum binding (MB).
3. To the remaining tubes were added the following, mixing well after each addition:
   a. 0.01 ml of patient's serum, or
   b. 0.01–0.1 ml of a standard hLTAA solution of varying concentrations such that a range of 10–100 nanograms of hLTAA is added to each tube.
   c. same as in 2a and 2b.

The tubes were rested at 4° C. for 16 hours, after which 0.05 ml of a 50% suspension of inactivated Staphylococcus aureus cells containing Protein A (Pansorbin, Chalbiochem-Behring Corp.) were added to each tube with mixing. The tubes again were rested at 4° C. for 1.5 hours, followed by centrifuging for 2 minutes at 12,000 rpm in a microcentrifuge. The supernatant was discarded, and the tip containing the pellet removed with a razor. The radioactive content of the pellet was measured by a gamma counter.

A standard curve was constructed using the values obtained with the hLTAA standard solutions by plotting the binding values for each standard against the log of its concentration. From this standard curve, the hLTAA concentration in each serum sample was interpolated from the individual binding values.

What is claimed is:

1. A substantially purified human lung tumor-associated antigen (hLTAA) associated with lung tumors comprising small cell carcinomas, large cell undifferentiated carcinomas, squamous cell carcinomas and adenocarcinomas, characterized by
   a diffusion coefficient ($D_{20,w}$) of $4.2$–$4.3 \times 10^{-7}$ $cm^2 sec^{-1}$, a sedimentation coefficient ($S_{20,w}$) of 4.5–4.6 S; and a Stokes radius of 51 Å;
   immunological reactivity with a xenoantiserum containing heterologous species antibodies raised in a heterologous species animal as an immune response to a crude extract of at least one of said lung tumors; and
   no antigenic cross-reactivity with $\alpha_1$-antichymotrypsin.

2. A method for the isolation and purification of the hLTAA of claim 1 from a crude extract of said lung tumor comprising complexing hLTAA with, and eluting hLTAA from, heterologous species antibodies directed against hLTAA in insolubilized form.

3. The method of claim 2, wherein the crude extract is pretreated by gel filtration and/or ion exchange chromatography.

4. Reagents for use in a serological immunoassay for the hLTAA of claim 1, comprising hLTAA and antibody specifically binding to hLTAA, wherein either the hLTAA or the antibody is fluorescent-, enzyme-, or radioisotope-labelled.

5. The reagent of claim 4, wherein the immunoassay is a radioimmunoassay and the assay mixture comprises radiolabelled hLTAA and unlabelled hLTAA antibody which specifically binds to hLTAA.

6. The reagent of claim 4 wherein the hLTAA is coupled to a solid support.

7. The reagent of claim 5, wherein the hLTAA is radiolabelled with radioactive iodine.

8. A reagent for use in lung cancer diagnosis comprising heterologous species antibodies which specifically bind to the hLTAA of claim 1.

9. The reagent of claim 8, wherein the antibodies are fluorescent-, enzyme-, or radio- isotope-labelled.

10. The reagent of claim 8, wherein the antibodies are coupled to a solid support.

11. A diagnostic kit for use in the diagnosis of lung cancer including a first container containing a reagent comprising unlabelled heterologous species antibodies and a second container containing a reagent comprising labelled heterologous species antibodies, said antibodies having binding specifically to the hLTAA of claim 1.

12. The kit of claim 11, wherein the unlabelled antibodies are coupled to a solid support.

13. The kit of claim 11, wherein the labelled and unlabelled antibodies are derived from two different heterologous species.

14. The kit of claim 11, wherein the unknown is a human serum sample.

15. The kit of claim 11, wherein the antibodies are radiolabelled with $^{125}I$.

16. A method for detecting the presence of the lung tumor antigen (hLTAA) of claim 1 in serum comprising interacting the serum or a fraction thereof with insolubilized anti-hLTAA antibody to bind hLTAA present in the serum to the antibody and form an antibody/antigen complex; interacting labelled anti-hLTAA antibody with this complex to form an antibody/antigen/-labelled antibody complex; and measuring the amount of labelled anti-hLTAA antibody in this complex.

17. A radioimmunoassay for determining the concentration of the hLTAA of claim 1 in an unknown comprising
    admixing with the unknown radiolabelled purified hLTAA and unlabelled antibody which specifically binds to hLTAA;
    after equilibrium is attained, recovering radiolabelled hLTAA complexed with antibody; and
    measuring the amount of radiolabelled hLTAA recovered and comparing it to a standard which correlates the amount of radiolabelled hLTAA recovered with the concentration of unlabelled competitor hLTAA in the unknown.

* * * * *